United States Patent [19]

Van de Sande et al.

[11] Patent Number: 4,537,853
[45] Date of Patent: Aug. 27, 1985

[54] PHOTOGRAPHIC SILVER HALIDE MATERIAL CONTAINING A BALLASTED ELECTRON-DONOR PRECURSOR COMPOUND

[75] Inventors: Christian C. Van de Sande, Belsele; André Verhecken, Mortsel; Wilhelmus Janssens, Aarschot, all of Belgium

[73] Assignee: Agfa-Gevaert, N.V., Mortsel, Belgium

[21] Appl. No.: 581,723

[22] Filed: Feb. 21, 1984

[30] Foreign Application Priority Data

Mar. 15, 1983 [EP]  European Pat. Off. ........ 83200353.7

[51] Int. Cl.³ .................... G03C 5/54; G03C 1/42; G03C 5/30; C07F 9/02
[52] U.S. Cl. .................................. 430/218; 430/440; 430/443; 430/505; 430/539; 430/566; 430/959; 430/955; 260/936; 568/12
[58] Field of Search ............... 430/218, 440, 443, 566, 430/959, 955, 505, 559; 260/936; 568/12

[56] References Cited

U.S. PATENT DOCUMENTS

| | | | |
|---|---|---|---|
| 2,953,591 | 9/1960 | Garner | 260/936 |
| 4,366,240 | 12/1982 | Lassig et al. | 430/218 |
| 4,371,604 | 2/1983 | Van de Sande et al. | 430/223 |
| 4,477,554 | 10/1984 | Van de Sande et al. | 430/223 |

FOREIGN PATENT DOCUMENTS 0038092 10/1981 European Pat. Off. .
0109701 5/1984 European Pat. Off. .

Primary Examiner—Richard L. Schilling
Attorney, Agent, or Firm—A. W. Breiner

[57] ABSTRACT

Photographic silver halide material containing a ballasted electron-donor precursor compound yielding by alkaline hydrolysis an electron-donor compound (ED-compound) capable (1) of donating electrons to an oxidized electron-accepting silver halide developing agent e.g. for scavenging it, said electron-donor precursor compound corresponding to the following general formula:

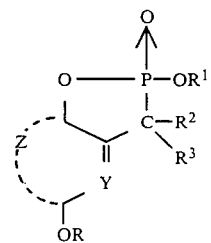

wherein:
R represents hydrogen or a substituent, e.g. an acyl group, which on hydrolytic removal allows the replacement of R by H,
$R^1$, $R^2$ and $R^3$ (same or different) are hydrocarbon substituents or $R^3$ is H, and
Z and Y represent the necessary atoms to close a benzene ring that may be substituted or form a fused ring system.

11 Claims, No Drawings

PHOTOGRAPHIC SILVER HALIDE MATERIAL CONTAINING A BALLASTED ELECTRON-DONOR PRECURSOR COMPOUND

The present invention relates to photographic silver halide material containing a novel ballasted electron-donor precursor compound (EDP-compound), which is capable of undergoing a cleavage reaction by alkaline hydrolysis to yield an electron-donor compound (ED-compound) capable of donating electrons to an electron-accepting oxidized silver halide developing agent.

ED-compounds may be used in non-photosensitive interlayers as scavenging agent for oxidized developer to avoid migration of oxidized developer from one photosensitive layer into another e.g. in multicolour silver halide photographic materials or play a role in silver halide emulsion layers of dye diffusion transfer materials as electron-donor for oxidized silver halide developing agent acting as electron transfer agent (ETA-compound).

The use of a scavenging compound is particularly advantageous in what is called now conventional multicolour silver halide photographic materials. Such materials contain three differently spectrally sensitive silver halide emulsion layers used for recording the primary colours, red, green and blue in the proportions in which they occur in the original object. The imagewise exposed silver halide in each emulsion layer is developed in a developer containing p-phenylene diamine or a derivative thereof. During the reduction of exposed silver halide to metallic silver the developing agent is oxidized and reacts with a so-called colour former or coupler to form the desired cyan, magenta or yellow dye image for subtractive colour reproduction.

In said multicolour material it is necessary to avoid migration of oxidized developer from one colour former containing layer into a neighbouring one since otherwise a false colour reproduction and colour fog spoiling the image will be produced.

The problem of false colour reproduction and colour fog is not only inherent to said conventional colour photography but is likewise associated with other multicolour reproduction systems operating with differently spectrally sensitized silver halide emulsion layers.

Important non-conventional multicolour reproduction systems are based on dye diffusion transfer processing. These systems are of particular value for reasons of simplicity of processing and rapidity of access to the colour image.

Dye diffusion transfer imaging can be carried out in a number of ways but each system is based on the same principle, namely the alteration of the solubility of dyes controlled by the development of the photographic silver image.

Most frequently the transferred dye-image is to be a positive image of the original.

Depending upon the type of silver halide emulsion used different kinds of dye providing systems are required to produce a positive transferred dye image.

If direct-positive silver halide emulsions are used positive image production with respect to the original requires that the dye providing system must yield (a) diffusible dye(s) in the non-exposed areas to an extent which is directly proportional to the degree of non-exposure. In a system fulfilling this requirement so-called diffusible dye releasing (DDR) compounds described e.g. in U.S. Pat. No. 3,227,550—U.S. Pat. No. 3,443,940 and U.S. Pat. No. 3,751,406 are used. Other suitable systems apply dye-releasing redox (DRR) compounds which cleave upon oxydation whereas their reduced state is stable to the processing conditions. When such DRR compounds are used in association with a developing silver halide emulsion of the direct-positive type cross-oxydation of the non-diffusible DRR compound with oxidized silver halide developer yields an alkali-labile oxidation product in the non-exposed areas only and hence a positive image-wise distribution of diffusible dye. Examples of image-wise cleaving DRR compounds are described in U.S. Pat. No. 3,628,952—G.B. Pat. No. 1,405,662—DE-OS No. 2,645,656 and Research Disclosures 12 832 (1974) and 15 157 (1976).

For image reversal with silver halide emulsions of the negative type the dye providing system should yield likewise diffusible dyes in the unexposed areas and progressively block the release of dye in the exposed areas depending on the degree of exposure. So-called dye-developers, e.g. those described in U.S. Pat. No. 2,983,606, are suitable for this purpose. These compounds are soluble in the alkaline processing fluids and hence are diffusible; in the exposed areas, however, cross-oxidation with oxidized silver halide developer will turn them into non-soluble, non-diffusible oxidation products.

According to another reversal process with silver halide emulsions of the negative type so-called IHO (Inhibited hydrolysis by oxydation) compounds can be used. The IHO compounds carry a ballast group and are initially immobile in the hydrophilic colloid layer wherein they are incorporated. Their main characteristic is that they are alkali-labile in reduced state so as to release a diffusible dye in the unexposed areas. In the exposed areas the IHO-compounds cross-oxidize with oxidized silver halide developer and are converted into their alkali-stable, still ballasted oxidized counterparts. Examples of IHO-compounds are described in DE-OS Nos. 2,402,900—2,543,902 and 2,654,213.

An alternative to these IHO-compounds for use with silver halide emulsions of the negative type are the IHR (Increased Hydrolysis by Reduction) compounds.

Said IHR-compounds are used in ballasted diffusion-resistant form and may be IHO-compounds in oxidized state or in general compounds wherefrom by reduction and hydrolysis in alkaline medium a diffusible photographically useful group (PUG) is released. The IHR-compounds react neither directly nor indirectly with oxidizing substances, e.g. the oxidation product of developers, so that their diffusion resistance at the exposed areas can not be changed. They are, however, capable of reacting with reducing compounds, e.g. by direct or indirect reaction with non-oxidized photographic developer which remains at the non-exposed areas of negative working silver-halide emulsion layers. By reduction a hydrolysable compound is obtained wherefrom a diffusion-mobile part being or including a photographically useful group e.g. dye or dye precursor is set free which is capable to diffuse into an image receiving layer where it is fixed.

In published EP-A No. 0.004 399 compounds are described that by reduction and hydrolysis yield quinone-methide compounds and a diffusible photographically useful group (PUG) e.g. a diffusible dye. This is illustrated by the following reaction scheme using simplified general formulae:

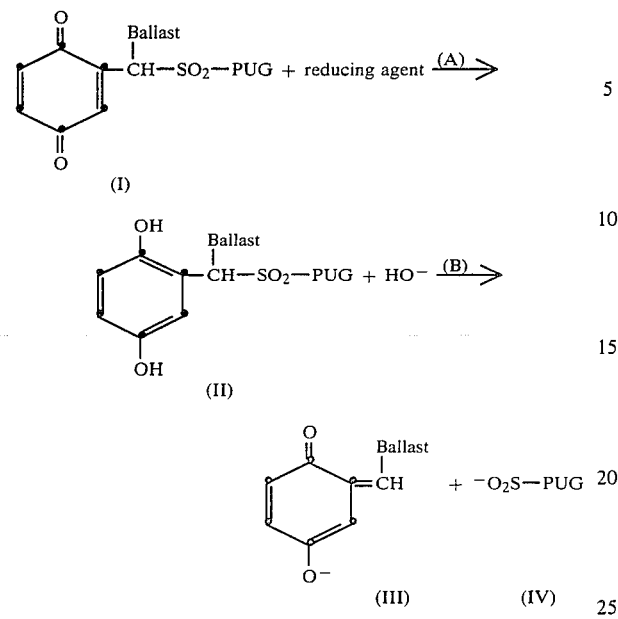

(I)

(II)

(III) (IV)

To compromise between so-called fog level and sufficient image-wise release of photographically useful substance within short processing times it would be advantageous to be able to control the reaction rate of the reactions of step (A) and/or (B). Experiments carried out showed that the reaction of step (B) under the alkaline conditions of silver halide development proceeds much faster than the reaction of step (A) and that some retardation of the reaction rate of reaction step (B) in order to avoid said fog would be welcome.

In a preferred embodiment the IHR-compounds are used in conjunction with an electron-donor compound (ED-compound) or electron donor-precursor compound (EDP-compound), and an electron-transfer agent (ETA) which is a compound that is a better silver halide reducing agent under the applied conditions of processing than the electron donor. On developing the silver halide the ETA-compound provides a corresponding pattern of oxidized electron donor because the oxidized ETA-compound readily accepts electrons from the ED-compound.

The PUG release operating with the ETA (developer) and ED-compound combination as explained above requires all reactions to proceed in the desired order to prevent the release of PUG-moieties in areas wherefrom it may not take place. The photographically useful group (PUG) has to be split off rapidly but also substantially inversely proportional to the concentration of photoexposed silver halide. In other words when processing an image-wise exposed silver halide emulsion of the negative type in operative association with the above quinonoid compound (I) and a reducing agent the diffusible PUG-substance should not be freed up to an unacceptable level in correspondence with the white areas of the photographed original or scene but should still be set free sufficiently rapidly in the less or non-exposed area where the concentration of reducing agent remained high. When the reduction of compound (I) with the reducing agent and the hydrolysis of compound (II) prevail over the reduction of the photoexposed silver halide, too large an amount of PUG-substance is split off in the area where it is not wanted. In the case where the PUG-substance is a dye an undesirable dye fog is obtained in the receptor element.

The ED-compound is used preferably in non-diffusible state in each silver halide emulsion layer whereas the ETA-compound is applied as diffusible developing agent.

The following general reaction scheme illustrates the reaction-relationship of photoexposed silver halide, ETA-compound, ED or EDP-compound and oxidized IHR-compound in aqueous alkaline medium.

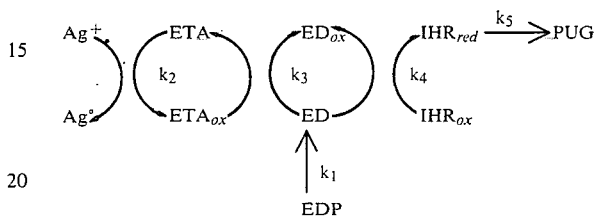

wherein:

$Ag^+$ is developable silver ion, $Ag^\circ$ is silver metal,

ETA is electron transfer agent, $ETA_{ox}$ is oxidized electron transfer agent,

EDP is electron donor precursor,

ED is electron donor, $ED_{ox}$ is oxidized electron donor, $IHR_{ox}$ is actually the IHR-compound comprising a ballasted carrier group linked to a releasable diffusible PUG-group by a cleavable group, $IHR_{red}$ is said $IHR_{ox}$ in reduced and cleavable state, PUG is a photographically useful group e.g. a dye moiety, and $k_1$, $k_2$, $k_3$, $k_4$ and $k_5$ are reaction rate constants obeying: $k_1 \simeq k_2 \simeq k_3 > k_4$.

Preferably $k_1$ and $k_2$ are equal, so that ED and $ETA_{ox}$ become available at the same rate. The rate constant $k_3$ is preferably about the same as or slightly greater than the rate constant $k_2$ so that there is no built up of excess $ETA_{ox}$.

The problem is to find EDP-compounds that sufficiently rapidly deblock to have $k_1 \simeq k_2$.

In the United Kingdom Patent Specification No. 1,596,828 an embodiment is described wherein alkali-labile electron donor precursors are employed for the reaction-rate-control of the release of a photographically useful group. The alkali-labile EDP-compounds are actually ED-compounds the active reducing site of which is blocked by a chemical substituent that can be removed by alkaline hydrolysis.

The IHR-compounds used in the process of said UK Patent Specification are immobile ballasted electron-accepting nucleophilic displacement (BEND) compounds which are capable of undergoing an intramolecular nucleophilic displacement reaction to release a diffusible photographically useful group (PUG) e.g. dye compound.

The dye release by said BEND-compounds is exemplified by the following reaction scheme using simplified general formulae:

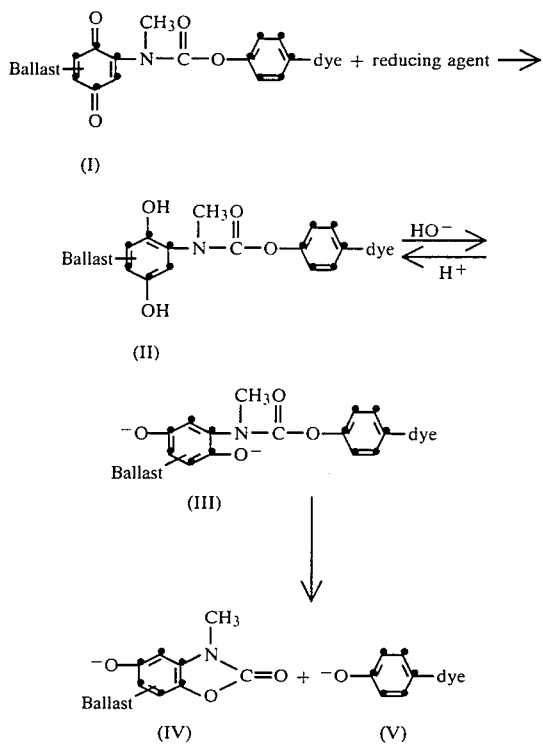

(I)

(II)

(III)

(IV)    (V)

The dye compound (V) is released where the nucleophilic group, here the hydroxyl group of the hydroquinone, can attack the carbamate ester linkage. However, when the nucleophilic group is oxidized, which is the case in the quinone form, nucleophilic displacement is impossible.

As is known in the art, "Ballast" stands for ballasting group, which group makes the molecule immobile in hydrophilic colloid layers when permeated by an alkaline aqueous liquid. Thus, said BEND-compounds are ballasted compounds capable of undergoing an electron-accepting nucleophilic displacement reaction separating hereby in alkaline medium a diffusible photographically useful moiety e.g. a dye.

The above BEND compounds and quinone-methide-yielding compounds are both IHR-compound the hydrolysability of which under alkaline conditions is increased by reduction.

It is an object of the present invention to provide novel electron-donor precursors the synthesis of which is very economical because it proceeds in good yield using in a one-step condensation reaction a phosphite ester and a hydroquinone-carbinol compound of the type already available for synthetising said IHO- and IHR-compounds.

It is an other object of the present invention to provide a photographic silver halide material for use in conventional as well as diffusion transfer photography, comprising one of said novel electron-donor precursors in at least one of its waterpermeable colloid layers.

Another object of the present invention is to provide a diffusion transfer image receiving material comprising a said EDP-compound.

It is more particularly an object of the present invention to provide a colour photographic silver halide material containing a plurality of differently spectrally sensitized silver halide emulsion layers and in an interlayer between two silver halide emulsion layers, a said novel electron-donor precursor in non-diffusing state.

It is further a particular object of the present invention to provide a photographic material suited for dye diffusion transfer imaging including in a water-permeable hydrophilic colloid medium: (1) photosensitive silver halide, (2) at least one immobile IHR-compound wherefrom a photographically useful group (PUG) can be released upon reduction by alkaline hydrolysis and (3) a combination of an ETA-compound and said novel EDP-compound offering an improvement in photographic sensitivity i.e. speed with a favourable relationship of maximum density ($D_{max}$) to minimum density ($D_{min}$) of the transferred PUG-compound e.g. a dye.

Other features and advantages of the invention will become apparent from the further description.

The novel electron donor precursors for use according to the present invention are within the scope of the following general formula (P):

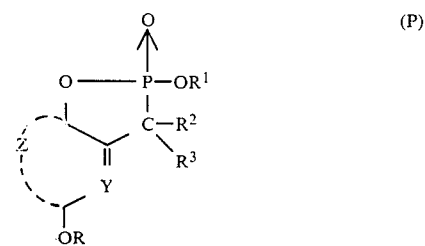

(P)

wherein:
R represents hydrogen or a substituent, e.g. an acyl group, which on hydrolytic removal allows the replacement of R by H,
$R^1$, $R^2$ and $R^3$ (same or different) represent a hydrocarbon group or substituted hdrocarbon group, e.g. a $C_1$–$C_{20}$ alkyl group, or $R^3$ represents hydrogen, and
Z and Y represent the necessary atoms to close a benzene ring substituted as indicated in the formula (P) but likewise such a benzene ring being further substituted e.g. with alkyl, alkoxy, or halogen, or Z and Y represent the necessary atoms to form a fused ring system including said benzene ring, at least one of $R^1$, $R^2$, $R^3$, Z and Y being or including a ballast group making said EDP-compound non-diffusing in a hydrophilic colloid layer when permeated by an alkaline aqueous liquid.

The present invention provides a photographic material comprising at least one layer containing light-sensitive silver halide and containing at least one ballasted electron-donor precursor compound (EDP-compound) which is capable of undergoing a cleavage reaction by alkaline hydrolysis to yield an electron-donor compound (ED-compound) capable of donating electrons to an electron-accepting oxidized silver halide developing agent, characterized in that said EDP-compound corresponds to the above general formula (P).

With regard to terminology used in the description of the present invention we like to point out that the term "non-diffusing" used herein has the meaning commonly applied to the term in photography and denotes materials that in any practical application do not migrate or wander through organic hydrophilic colloid layers, e.g. gelatin, when permeated with an alkaline aqueous liquid. The same meaning is to be attached to the term "immobile".

The term "diffusing" as applied to the materials of this invention has the converse meaning and denotes materials having the property of diffusing effectively through the colloid layers of the photographic elements in an alkaline aqueous liquid. "Mobile" has the same meaning.

The photographically useful group "PUG" that is released may provide, e.g. a dye, a dye precursor, ultraviolet light absorbing compound, fog inhibiting compound, development retarding compound, silver halide fixing agent, gelatin hardening agent, development accelerator or silver halide fogging agent.

The preparation of these EDP-compounds can proceed according to the following reaction scheme:

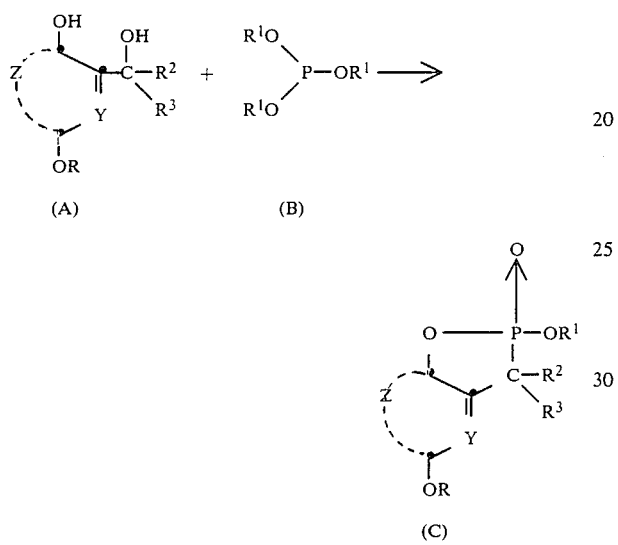

The preparation of suitable carbinol compounds (A) is described e.g. in the G.B. Pat. No. 1,593,669, in the published European Patent Application No. 00 38 092, and in the EP-A No. 83.201506.

A particularly useful group of ED-precursor compounds according to the present invention corresponds to the following general formula (Q):

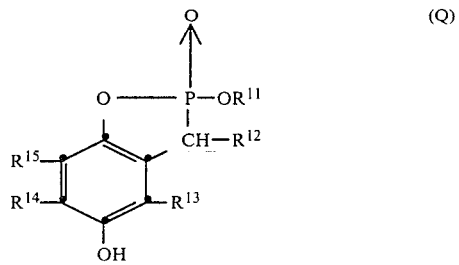

wherein:
$R^{11}$ represents a hydrocarbon group or a substituted hydrocarbon group e.g. an alkyl or an aryl group, and each of $R^{12}$, $R^{13}$, $R^{14}$ and $R^{15}$ (same or different) represents a hydrocarbon group or a substituted hydrocarbon group e.g. an alkyl or an aryl group, or halogen atom e.g. chlorine or an alkoxy group, or at least one of $R^{13}$, $R^{14}$ and $R^{15}$ represents hydrogen, or $R^{14}$ and $R^{15}$ together represent the necessary atoms to form a fused homocyclic ring or such ring in substituted form e.g. substituted with non-ionic substituents, at least one of $R^{11}$ to $R^{15}$ containing a carbon chain of at least 8 carbon atoms e.g. 8–20 C atoms.

Representatives of these ED-precursor compounds are listed in the following Table 1.

TABLE 1

| EDP compound | $R^{11}$ | $R^{12}$ | $R^{13}$ | $R^{14}$ | $R^{15}$ |
|---|---|---|---|---|---|
| 1 | $C_2H_5$ | $CH_3$ | —⟨phenyl⟩—O—Cet | $CH_3$ | H |
| 2 | " | n-$C_{13}H_{27}$ | H | $CH_3$ | $CH_3$ |
| 3 | " | $CH_3$ | —⟨phenyl⟩—O—Cet | —$(CH_2)_4$— | |
| 4 | " | n-$C_{13}H_{27}$ | n-propyl | " | |
| 5 | " | " | " | —$(CH_2)_3$—CH— | $CH_3$ |
| 6 | " | " | " | $CH_3$ | H |
| 7 | " | $CH_3$ | —⟨phenyl⟩—O—Cet | H | H |
| 8 | " | n-$C_{13}H_{27}$ | n-propyl | $CH_3$ | Cl |
| 9 | " | " | H | $CH_3$ | $CH_3$ |
| 10 | " | " | " | $CH_3$ | H |
| 11 | " | n-$C_{17}H_{35}$ | n-propyl | H | H |
| 12 | " | " | Cl | H | H |
| 13 | " | $CH_3$ | —⟨phenyl⟩—O—Cet | $CH_3$ | $CH_3$ |
| 14 | " | " | " | H | H |

TABLE 1-continued

| EDP compound | R$^{11}$ | R$^{12}$ | R$^{13}$ | R$^{14}$ | R$^{15}$ |
|---|---|---|---|---|---|
| 15 | phenyl | " | " | —(CH$_2$)$_4$— | |
| 16 | CH$_3$ | " | " | " | |
| 17 | iso-octyl | " | " | " | |
| 18 | n-C$_8$H$_{17}$ | " | phenyl-OCH$_3$ | H | H |
| 19 | " | " | phenyl-O—Cet | —(CH$_2$)$_4$— | |
| 20 | n-C$_{10}$H$_{21}$ | " | " | " | |
| 21 | n-C$_6$H$_{13}$ | " | " | " | |
| 22 | t-C$_4$H$_9$ | " | " | " | |
| 23 | —CH$_2$-phenyl | " | " | " | |
| 24 | n-C$_5$H$_{11}$ | " | " | " | |
| 25 | —CH$_2$—t-C$_4$H$_9$ | " | " | " | |
| 26 | —CH$_2$-(bicyclic) | " | " | " | |
| 27 | phenyl-t-C$_4$H$_9$ | " | " | " | |
| 28 | naphthyl | " | " | " | |
| 29 | —CH(C$_4$H$_9$)$_2$ | " | " | " | |
| 30 | —(CH$_2$)$_2$—O—phenyl—C(CH$_3$)$_2$—CH$_2$—t-C$_4$H$_9$ | " | " | " | |

Cet = n-hexadecyl

The present invention includes also ED-precursor compounds having a duplo-structure as represented by the following general formula (R):

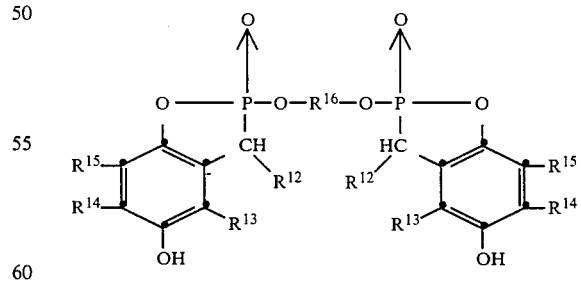

Particularly useful ED-precursor compounds according to general formula (R) are listed in table 2.

TABLE 2

| EDP compound | R$^{12}$ | R$^{13}$ | R$^{14}$ | R$^{15}$ | R$^{16}$ |
|---|---|---|---|---|---|
| 31 | CH$_3$ | phenyl-OCet | —(CH$_2$)$_4$— | | —CH$_2$-(bicyclic)-CH$_2$— |

TABLE 2-continued

| EDP compound | $R^{12}$ | $R^{13}$ | $R^{14}$ | $R^{15}$ | $R^{16}$ |
|---|---|---|---|---|---|
| 32 | " | " | " |  | $-(CH_2)_6-$ |
| 33 | " | " | " |  | $-(CH_2)_2-$ |

The following preparation 1 of EDP-compound 3 is illustrative for the preparation of the EDP-compounds according to the present general formulae (P) and (Q).

PREPARATION 1

262 g of 2(1'-hydroxyethyl)3-p-n-hexadecyloxyphenyl-5,6-tetramethylene hydroquinone (0.5 mole) and 125 ml of triethyl phosphite (0.725 mole) were melted together whereby ethanol was distilling off. When the temperature of the reaction mixture reached 150° C. the distillation stopped and the reaction mixture was kept for 30 min at that temperature. Thereupon it was cooled down to 70° C. whereupon 2 l of n-hexane were added. On further cooling a creamy precipitate was obtained. The precipitate was separated by suction filtering, washed with n-hexane and dried. 240 g of a faint yellow coloured product were obtained, melting point: 82° C. The purification proceeded by recrystallizing from 1.7 l of n-hexane. Melting point: 88° C. Purifying of other EDP-compounds can proceed by preparative column chromatography using a mixture of $CH_2Cl_2$/ethylacetate (95/5 by volume) as an eluent if recrystallization is ineffective.

The following preparation 2 of EDP-compound 31 is illustrative for the preparation of the duplo-EDP-compounds according to general formula (R).

PREPARATION 2

Into a 3-necked reaction flask of 500 ml provided with a stirrer, a Liebig's condenser, an air-cooler having at the top a thermometer, and a thermometer for dipping into the reaction mixture were introduced:

120 g of compound 3 of table 1 and 100 ml of xylene. By heating a clear solution was obtained whereto 20 g of dihydroxymethyl(5,2,1,0$^{2,6}$)tricyclodecane, prepared as described in published EP-A No. 0084 694, were added. Thereupon the reaction flask was placed in an oil bath kept at 190° C. At the top of the air-cooler the ethanol being splitted off in the condensation reaction distilled. The temperature of the reaction mixture rose to 160° C.

After a reaction period of 10 h the xylene was removed by evaporation under diminished pressure. The residue was purified by column-chromatography using as stationary phase material silica with average grain size smaller than 0.08 mm and as eluent a mixture of methylene chloride and ethyl acetate (90/10 by volume). Yield: 28.7 g of pure compound 31.

The EDP-compounds can be used in any conventional photographic colour material and in any diffusion transfer material as described hereinbefore.

The EDP-compounds are according to a preferred embodiment used in dye diffusion transfer materials containing IHR-compounds. They are incorporated in such materials in immobile form together with the immobile IHR-compound e.g. the EDP-compound is co-dispersed with the IHR-compound in the same hydrophilic colloid layer.

In a diffusion transfer material e.g. containing a said IHR-compound the present EDP-compounds are preferably used in conjunction with a diffusible electron transfer agent (ETA-compound).

Typically useful ETA-compounds include hydroquinone compounds, aminophenol compounds, catechol compounds, phenylene diamines and 3-pyrazolidinone compounds e.g. 1-aryl-3-pyrazolidinone as defined e.g. in U.S. Pat. No. 4,139,379.

A combination of different ETA's such as those disclosed in U.S. Pat. No. 3,039,869 can also be employed. Such developing agents can be employed in the liquid processing composition or may be contained, at least in part, in any layer or layers of the photographic element or film unit such as the silver halide emulsion layers, the dye image-providing material layers and/or interlayers, but is used preferably in diffusible form in a non-sensitive hydrophilic colloid layer adjacent to at least one silver halide emulsion layer or image-receiving layer. The particular ETA selected will, of course, depend on the particular electron donor precursor and IHR-compound used in the process and the processing conditions for the particular photographic element.

Migration of non-oxidized developing agent, e.g. acting as ETA-compound, proceeds non-image-wise and will have an adverse effect on correct colour rendering when surplus developing agent remains unoxidized in the photoexposed area of a negative working emulsion layer. Therefore, according to a preferred embodiment of the present invention a silver halide solvent e.g. thiosulphate is used to mobilize unexposed silver halide in complexed form for helping to neutralize (i.e. oxidize by physical development) migrated developing agent in the photoexposed area wherein unaffected (ETA-compound) should no longer be available. The use of silver halide solvents for that purpose has been described in the published EP-A No. 0049002.

In order to obtain a more correct colour rendition in dye diffusion transfer materials it is also advantageous to prevent oxidized ETA-compound from migrating to adjacent imaging layers. For the interception so-called scavengers can be used that are incorporated in the photographic material in non-diffusible state in interlayers between the imaging layers. Suitable scavengers for that purpose are described e.g. in U.S. Pat. Nos. 4,205,987—4,192,678—4,192,679; G.B. Pat No. 2,081,463; German Offenlegungsschrift (DE-OS) No. 2,908,874 Research Disclosure, February 1979, item 17842 and EP No. 29546. The present EDP-compounds can likewise be used as scavenger precursors.

A preferred colour photographic silver halide material suited for dye diffusion transfer imaging according to the present invention comprises a support carrying at least one alkali-permeable silver halide hydrophilic colloid emulsion layer which contains the present EDP-compound and an IHR-compound which is immobile in an alkali-permeable colloid medium when contacted with an alkaline liquid and which contains a dye moiety and a ballast group, said IHR-compound being capable of being reduced by a silver halide developing agent and in reduced state being capable of releasing said dye moiety by alkaline hydrolysis.

In an embodiment for producing multicolour images by dye diffusion transfer this invention relates to photographic materials that comprise a support carrying (1) a red-sensitive silver halide emulsion layer having operatively associated therewith a said EDP-compound and a IHR-compound that is initially immobile in an alkali-permeable colloid medium and wherefrom through the reducing action of a silver halide developing agent and alkalinity a cyan dye is split off in diffusible state, (2) a green-sensitive silver halide emulsion layer having operatively associated therewith a said EDP-compound and a said IHR-compound with the difference that a magenta dye is split off in diffusible state, and (3) a blue-sensitive silver halide emulsion layer having operatively associated therewith a said EDP-compound and a said IHR-compound with the difference that a yellow dye is split off in diffusible state.

The image dye-providing moiety may be a preformed dye or a shifted dye. Dye materials of this type are well-known in the art and include azo dyes, azomethine (imine) dyes, anthraquinone dyes, alizarine dyes, merocyanine dyes, quinoline dyes, cyanine dyes and the like. The shifted dyes include those compounds whose light-absorption characteristics are shifted hypsochromically or bathochromically when subjected to a different environment such as a change in pH, a reaction with a material to form a complex, a tautomerization, reactions to change the pKa of the compound, a removal of a group such as a hydrolysable acyl group connected to an atom of the chromophore as mentioned e.g. in U.S. Pat. No. 3,260,597 of Water J. Weyerts and Wilho M. Salminen, issued July 12, 1966. In certain embodiments, the shifted dyes are highly preferred, especially those containing a hydrolyzable group on an atom affecting the chromophore resonance structure, since the compounds can be incorporated directly in a silver halide emulsion layer or even on the exposure side thereof without substantial reduction in the light that is effective in the exposure of the silver halide. After exposure, the dye can be shifted to the appropriate colour such as, e.g., by hydrolytic removal of an acyl group to provide the respective image dye.

The IHR compounds and EDP-compounds for use according to the invention are incorporated in the coating liquid for the layers of a photographic material by one of the usual methods. The quantity of IHR-compound(s) used per liter of coating liquid varies within relatively wide limits e.g. dependent on the photographically useful group that is to be split off and the most suitable concentration can be found with the aid of simple tests. For example, from 0.01 to 10 g, preferably from 0.1 to 0.5 g, of IHR compound may be used per sq.m. The incorporation into the coating liquid e.g. the silver halide emulsion may proceed, from a dispersion prepared in a sand-mill or by using ultrasound.

The concentration of EDP-compound in the photographic material may vary within a broad range but is, e.g., in the molar range of 1:1 to 8:1 with respect to the IHR-compound.

According to another method, it may be desired to incorporate an IHR compound in a hydrophilic colloid layer in the form of so-called mirco-capsules together with silver halide and the EDP-compound. In that case, two or more differently sensitized light-sensitive silver halide emulsions and the appropriate diffusion resistant compounds may be combined in a single layer in the form of so-called mixed grain emulsions, for example as described in U.S. Pat. No. 2,698,794 of Leopold Godowsky, issued Jan. 4, 1955. Methods of incorporation in which an IHR compound is incorporated into a hydrophilic binder from an alkaline aqueous solution may be applied too since there is no danger of hydrolysis of the compound In a particular embodiment said IHR-compound and EDP-compound are present in a hydrophilic colloid layer adjacent to a silver halide emulsion layer, this adjacent layer being preferably situated behind, viewed in the direction of incident light during exposure, the silver halide emulsion layer.

In a specific embodiment in accordance with this invention a photographic material being a film unit is provided that is adapted to be processed by passing said unit between a pair of juxtaposed pressure-applying members, such as would be found in a camera designed for in-camera processing. The unit comprises (1) a photosensitive element, which contains at least one silver halide emulsion layer including a said EDP and IHR compound that is initially immobile in an alkali-permeable colloid medium and wherefrom through the reducing action of a silver halide developing agent and alkalinity a dye is split off in diffusible state, (2) an image dye-receiving layer, (3) means for discharging an alkaline processing composition within the film unit such as a rupturable container, which is adapted to be positioned during processing of the film so that a compressive force applied to the container by the pressure-applying members will effect a discharge of the container's contents within the film, and (4) a silver halide developing agent, which is soluble in the alkaline processing composition located within said film unit.

The photographic material of the present invention is useful in a process comprising (1) applying an alkaline processing composition to the image-wise exposed photographic material comprising a support carrying at least one silver halide emulsion layer and at least one alkali-permeable layer (which may be the same layer as the one containing the silver halide) comprising said EDP-compound and said IHR-compound that is reduced and by alkaline hydrolysis releases a dye, and (2) allowing the diffusion with said alkaline processing composition of the dye out of the layer in which it was originally incorporated to have it introduced imagewise in another non-light-sensitive layer acting as receptor layer.

For in-camera processing the photosensitive material is preferably composed such that the photosensitive silver halide emulsion layer(s) is (are) negative-working and applied to the same support as the receptor layer so as to form an integral combination of light-sensitive layer(s) and a non light-sensitive image receiver part containing an opaque layer, which is alkali-permeable, reflective to light and located between the receptor layer and the silver halide emulsion layer(s).

In a colour photographic element according to the invention for in-camera-processing containing two or more silver halide emulsion layers, each silver halide emulsion layer containing a dye image-providing material or having the dye image-providing material present in a contiguous layer may be separated from the other silver halide emulsion layer(s) in the film unit by (an) interlayer(s), including e.g. gelatin, calcium alginate, or any of the colloids disclosed in U.S. Pat. No. 3,384,483 of Richard W. Becker, issued May 21, 1968, polymeric materials such as polyvinylamides as disclosed in U.S. Pat. No. 3,421,892 of Lloyd D. Taylor, issued Jan. 14, 1969, or any of those disclosed in French Patent Specification No. 2,028,236 filed Jan. 13, 1970 by Polaroid Corporation or U.S. Pat. Nos. 2,992,104 of Howard C. Haas, issued July 11, 1961 and 3,427,158 of David P. Carlson and Jerome L. Reid, issued Feb. 11, 1969.

According to an embodiment in the preparation of a multicolour diffusion transfer material according to the present invention, a water-permeable colloid interlayer dyed with a yellow non-diffusing dye or Carey Lea silver is applied to shield the green- and red-sensitized emulsion layers from exposure to blue light.

In certain embodiments of the invention and especially with integral format film units, an opacifying agent can be applied from a processing composition. Examples of opacifying agents include carbon black, barium sulphate, zinc oxide, barium stearate, silicates, alumina, zirconium oxide, zirconium acetyl acetate, sodium zirconium sulphate, kaolin, mica, titanium dioxide, organic dyes such as indicator dyes, nigrosines, or mixtures thereof in widely varying amounts depending upon the degree of capacity desired. In general, the concentration of opacifying agent should be sufficient to prevent further exposure of the silver halide emulsion or emulsions of the film unit by ambient actinic radiation through the layer of processing composition, either by direct exposure through a support or by light piping from the edge of the element. For example, carbon black or titanium dioxide will generally provide sufficient opacity when they are present in the processing solution in an amount of from about 5 to 40% by weight. After the processing solution and opacifying agent have been distributed into the film unit, processing may take place out of the camera in the presence of acitinic radiation in view of the fact that the silver halide emulsion(s) of the laminate is (are) appropriately protected against incident radiation, at one major surface by the opaque processing composition and at the remaining major surface by the opaque layer that is permeable to alkaline solutions. In certain embodiments, ballasted indicator dyes or dye precursors can be incorporated in a layer on the exposure side of the photosensitive layers; the indicator dye is preferably transparent during exposure and becomes opaque when contacted with the processing composition. Opaque binding tapes can also be used to prevent edge leakage of actinic radiation incident on the silver halide emulsion.

When titanium dioxide or other white pigments are employed as the opacifying agent in the processing composition, it may also be desirable to employ in cooperative relationship therewith a pH-sensitive opacifying dye such as a phthalein dye. Such dyes are light-absorbing or coloured at the pH at which image formation is effected and colourless or not light-absorbing at a lower pH. Other details concerning these opacifying dyes are described in French Patent Specification No. 2,026,927 filed Dec. 22, 1969 by Polaroid Corporation.

The substantially opaque, light-reflective layer, which is permeable to alkaline solutions, in the integral receiver film units of the present invention can generally comprise any opacifier dispersed in a binder as long as it has the desired properties. Particularly desirable are white light-reflective layers since they present esthetically pleasing backgrounds on which to view a transferred dy image and also possess the optical properties desired for reflection of incident radiation. Suitable opacifying agents include, as already mentioned with respect to the processing composition, titanium dioxide, barium sulphate, zinc oxide, barium stearate, silver flake, silicates, alumina, zirconium oxide, zirconium acetyl acetate, sodium zirconium sulphate, kaolin, mica, or mixtures thereof in widely varying amounts depending upon the degree of opacity desired. The opacifying agents may be dispersed in any binder such as an alkaline solution-permeable polymeric matrix such as, for example, gelatin, polyvinyl alcohol, and the like. Brightening agents such as the stilbenes, coumarins, triazines and oxazoles may also be added to the light-reflective layer, if desired. When it is desired to increase the opacifying capacity of the light-reflective layer, dark-coloured opacifying agents may be added to it, e.g., carbon black, nigrosine dyes, etc. Another technique to increase the opacifying capacity of the light-reflective layer is to employ a separate opaque layer underneath it comprising, e.g., carbon black, nigrosine dyes, etc., dispersed in a polymeric matrix that is permeable to alkaline solutions such as, e.g., gelatin, polyvinyl alcohol, and the like. Such an opaque layer would generally have a density of at least 4 and preferably greater than 7 and would be substantially opaque to actinic radiation. The opaque layer may also be combined with a developer scavenger layer if one is present. The light-reflective and opaque layers are generally 0.025 to 0.15 mm in thickness, although they can be varied depending upon the opacifying agent employed, the degree of opacity desired, etc.

The photosensitive substances used in this invention are preferably silver halide compositions and may comprise silver chloride, silver bromide, silver bromoiodide, silver chlorobromoiodide and the like, or mixtures thereof. The emulsions may be coarse- or fine-grain and can be prepared by any of the well-known procedures, e.g., single-jet emulsions, double-jet emulsions, such as Lippmann emulsions, ammoniacal emulsions, thiocyanate- or thioether-ripened emulsions such as those described in U.S. Pat. Nos. 2,222,264 of Adolph H. Nietz and Frederick J. Russel, issued Nov. 19, 1940, 3,320,069 of Bernard D. Illingsworth, issued May 16, 1967, and 3,271,157 of Clarence E. McBride, issued Sept. 6, 1966. Surface-image emulsions may be used or interal-image emulsions may be used such as those described in U.S. Pat. Nos. 2;592,250 of Edward Philip Davey and Edward Bowes Knott, issued Apr. 8, 1952, 3,206,313 of Henry D. Porter, Thomas H. James and Wesley G. Lowe, issued Sept. 14, 1965, and 3,447,927 of Robert E. Bacon and Jean F. Barbier, issued June 3, 1969. The emulsions may be regular-grain emulsions such as the type described by Klein and Moisar in J.Photogr.Sci., Vol. 12, No. 5, September/October, 1964, pp. 242-251. If desired, mixtures of surface- and internal-image emulsions may be used as described in U.S. Pat. No. 2,996,382 of George W. Luckey and John C. Hoppe, issued Aug. 15, 1961.

Negative-type silver halide emulsions are normally but likewise direct-positive emulsions may be used such as those described in U.S. Pat. Nos. 2,184,013 of John A. Leermakers, issued Dec. 19, 1939, 2,541,472 of William B. Kendall and George D. Hill, issued Feb. 13, 1951, 3,367,778 of Robert W. Berriman, issued Feb. 6, 1968, 3,501,307 of Bernard D. Illingsworth, issued Mar. 17, 1970, 2,563,785 of Charles F. Ives, issued Aug. 7, 1951, 2,456,953 of Edward Bowes Knot and Guy William Willis, issued Dec. 21, 1948, 2,861,885 of Edwin H. Land, issued Nov. 25, 1958, 3,761,276 of Francis John Evans, issued Sept. 25, 1973, 3,761,266 of Kirby Mitchell Milton, issued Sept. 25, 1973, 3,736,140 of Susan Starr Collier and Paul Brewster Gilman Jr., issued May 29, 1973, and 3,730,723 of Paul Brewster Gilman Jr., Ronald George Raleigh and Thaddeus Donald Koszelak, issued May 1, 1973, and U.K. Patent Specification No. 723,019 filed Feb. 5, 1952 by Gevaert Photo-Producten N.V.

Silver halide emulsions useful in our invention are well-known to those skilled in the art. More details about their composition, preparation and coating are described, e.g., in Product Licensing Index, Vol. 92, December 1971, publication 9232, p. 107–109.

According to one embodiment, the silver halide emulsion layers in the invention comprise photosensitive silver halide dispersed in gelatin and are about 0.2 to 2 μm thick; the dye image-providing materials are dispersed in a polymeric binder permeable to alkaline solutions, such as gelatin, to form a separate layer of about 1 to 7 μm thick, in combination with polymeric interlayers permeable to alkaline solutions, e.g., gelatin, being about 1 to 5 μm thick. Of course, these thicknesses are approximate only and may be modified according to the product desired.

The support for the photographic elements of this invention may be any material as long as it does not deleteriously affect the photographic properties of the film unit and is dimensionally stable. Typical flexible sheet materials are paper supports, e.g. coated at one or both sides with an α-olefin polymer, e.g. polyethylene; they include cellulose nitrate film, cellulose acetate film, poly(vinyl acetal) film, polystyrene film, poly(ethylene terephthalate) film, polycarbonate film, poly-α-olefins such as polyethylene and polypropylene film, and related films or resinous materials. The support is usually about 0.05 to 0.15 mm thick.

For use in colour photography any material can be employed as the image-receiving layer as long at the desired function of mordanting or otherwise fixing the diffused dye will be obtained. The particular material chosen will, of course, depend upon the dye to be mordanted. If acid dyes are to be mordanted, the image-receiving layer can be composed of or contain basic polymeric mordants such as polymers of amino-guanidine derivatives of vinyl methyl ketone such as described in U.S. Pat. No. 2,882,156 of Louis M. Minsk, issued Apr. 14, 1959, and basic polymeric mordants and derivatives, e.g. poly-4-vinylpyridine, the 2-vinylpyridine polymer metho-p-toluene sulphonate and similar compounds described in U.S. Pat. No. 2,484,430 of Robert H. Sprague and Leslie G. Brooker, issued Oct. 11, 1949, the compounds described in the published German Patent Application No. 2,200,063 filed Jan. 11, 1971 by Agfa-Gevaert A.G. Suitable mordanting binders include, e.g. guanylhydrazone derivatives of actyl styrene plymers, as described e.g. in published German Patent Specification No. 2,009,498 filed Feb. 28, 1970 by Agfa-Gevaert A.G. In general, however, other binders, e.g. gelatin, would be added to the last-mentioned mordanting binders. Effective mordanting compositions are long-chain quaternary ammonium or phosphonium compounds or ternary sulphonium compounds. e.g. those described in U.S. Pat. Nos. 3,271,147 of Walter M. Bush and 3,271,148 of Keith E. Whitmore, both issued Sept. 6, 1966, and cetyltrimethyl-ammonium bromide. Certain metal salts and their hydroxides that form sparingly soluble compounds with the acid dyes may be used too. The dye mordants are dispersed in one of the usual hydrophilic binders in the image-receiving layer, e.g., in gelatin, polyvinylpyrrolidone or partly or completely hydrolysed cellulose esters.

Generally, good results are obtained when the image-receiving layer, which is preferably permeable to alkaline solution, is transparent and about 4 to about 10 μm thick. This thickness, of course, can be modified depending upon the result desired. The image-receiving layer may also contain ultraviolet-absorbing materials to protect the mordanted dye images from fading, brightening agents such as the stilbenes, coumarins, triazines, oxazoles, dye stabilizers such as the chromanols, alkyl-phenols, etc.

Use of pH-lowering material in the dye-image-receiving element of a film unit according to the invention will usually increase the stability of the transferred image. Generally, the pH-lowering material will effect a reduction of the pH of the image layer from about 13 or 14 to at least 11 and preferably 5 to 8 within a short time after inbibition. For example, polymeric acids as disclosed in U.S. Pat. No. 3,362,819 of Edwin H. Land, issued Jan. 9, 1968 or solid acids or metallic salts, e.g. zinc acetate, zinc sulphate, magnesium acetate, etc., as disclosed in U.S. Pat. No. 2,584,030 of Edwin H. Land, issued Jan. 29, 1952, may be employed with good results. Such pH-lowering materials reduce the pH of the film unit after development to terminate development and substantially reduce further dye transfer and thus stabilize the dye image.

An inert timing or spacer layer may be employed in practice over the pH-lowering layer, which "times" or controls the pH reduction depending on the rate at which alkali diffuses through the inert spacer layer. Examples of such timing layers include gelatin, polyvinyl alcohol or any of the colloids disclosed in U.S. Pat. No. 3,455,686 of Leonard C. Farney, Howard G. Rogers and Richard W. Yound, issued July 15, 1969. The timing layer may be effective in evening out the various reaction rates over a wide range of temperatures, e.g., premature pH reduction is prevented when inbibition is effected at temperatures above room temperature, e.g. at 35° to 37° C. The timing layer is usually about 2.5 μm to about 18 μm thick. Especially good results are obtained when the timing layer comprises a hydrolysable polymer or a mixture of such polymers that are slowly hydrolysed by the processing composition. Examples of such hydrolyable polymers include polyvinyl acetate, polyamides, cellulose esters, etc.

The present invention includes the embodiment wherein the EDP-compound according to general formula (P) is present in a water-permeable binder layer of an image-receiving material useful in diffusion-transfer-reversal (DTR-) processing with exposed silver halide emulsion layer(s). It has been established experimentally that besides the desired reduction of oxidized developing agent (ETA-compound) the presence of said EDP-compound has a favourable influence on the colour fastness of the dye images especially with respect to the cyan dyes of the azo dye type used in dye diffusion transfer processes.

An alkaline processing composition employed in this invention can be a conventional aqueous solution of an alkaline material, e.g. sodium hydroxide, sodium carbonate or an amine such as diethylamine, preferably possessing a pH beyond 11.

According to one embodiment the alkaline processing liquid contains the diffusible developing agent (ETA-compound) that effects the reduction of the silver halide, e.g. ascorbic acid or a 3-pyrazolidinone developing agent e.g. 1-phenyl-4-methyl-3-pyrazolidinone.

The alkaline processing composition employed in this invention may also contain a desensitizing agent such as methylene blue, nitro-substituted heterocyclic compounds and 4,4'-bipyridinium salts to insure that the photosensitive element is not further exposed after it is removed from the camera for processing.

The solution also preferably contains a viscosity-increasing compound such as a high-molecular-weight polymer, e.g. a water-soluble ether inert to alkaline solutions such as hydroxyethylcellulose or alkali metal salts of carboxymethylcellulose such as sodium carboxymethylcellulose. A concentration of viscosity-increasing compound of about 1 to about 5% by weight of the processing composition is preferred. It will impart thereto a viscosity of about 100 mPa.s to about 200,000 mPa.s.

Processing may proceed in a tray developing unit as is present, e.g., in an ordinary silver complex diffusion transfer (DTR) apparatus in which the contacting with a separate dye image-receiving material is effected after a sufficient absorption of processing liquid by the photographic material has taken place. A suitable apparatus for said purpose is the COPYPROOF CP 38 DTR-developing apparatus. COPYPROOF is a trade name of Agfa-Gevaert, Belgium/Germany.

According to other embodiments wherein the image-receiving layer is integral with the photosensitive layer(s) the processing liquid is applied from a rupturable container or by spraying.

The rupturable container that may be employed in this invention may be of the type disclosed in U.S. Pat. Nos. 2,543,181 of Edwin H. Land, issued Feb. 27, 1951, 2,643,886 of Ulrich L. di Ghilini, issued June 30, 1953, 2,653,732 of Edwin H. Land, issued Sept. 29, 1953, 2,723,051 of William J. McCune Jr., issued Nov. 8, 1955, 3,056,492 and 3,056,491, both of John E. Campbell, issued Oct. 2, 1962, and 3,152,515 of Edwin H. Land, issued Oct. 13, 1964. In general such containers comprise a rectangular sheet of fluid- and air-impervious material folded longitudinally upon itself to form two walls that are sealed to one another along their longitudinal and end margins to form a cavity in which processing solution is contained.

While the alkaline processing composition used in this invention can be employed in a rupturable container, as described previously, to facilitate conveniently the introduction of processing composition into the film unit, other means of discharging processing composition within the film unit could also be employed, e.g., means injecting processing solution with communicating members similar to hypodermic syringes, which are attached either to a camera cartridge, as described in U.S. Pat. No. 3,352,674 of Donald M. Harvey, issued Nov. 14, 1967.

As is clear from the preceding, IHR-compounds have particular application in a diffusion transfer process where it is desired to have a dye or dye precursor entity transferred to an adjacent layer or a receiving element. However, in certain embodiments this invention relates to the release of an image-wise distribution of a diffusible photographically useful compound, which is not a dye or dye precursor but a photographic reagent. Typical useful photographic reagents are known in the art, such as in U.S. Pat. Nos. 3,227,551 of Charles R. Barr, John Williams and Keith Whitmore, issued Jan. 4, 1966; 3,364,022 of Charles R. Barr, issued Jan. 16, 1968; 3,379,529 of Ralph Frederik Porter, Judith A. Schwan and John W. Gates, issued Apr. 23, 1968 and 3,698,898 of J. Michael Grasshoff and Lloyd D. Taylor, issued Oct. 17, 1972, e.g. a silver-complexing agent acting as a silver halide solvent, a fixing agent, a toning agent, a hardener, an antifogging agent, a sensitizer, a desensitizer, a developer, an oxidizing agent, a developing inhibitor or restrainer.

The silver halide development inhibitor includes e.g. triazoles and tetrazoles such as a 5-mercapto-1-phenyl-tetrazole, a 5-methylbenzotriazole, a 4,5-dichlorobenzotriazole and the like. The antifoggant includes besides these mercapto compounds e.g. azaindenes such as a tetrazaindene and the like.

The following examples further illustrate the invention, particularly with respect to dye diffusion transfer, but the invention is not limited thereto. All percentages and ratios are by weight, unless otherwise mentioned.

In the following examples reference is made to a colour providing compound. The invention, however, is not at all limited to this aspect and it should be kept in mind that for various other purposes other photographically useful fragments may be present in these compounds instead of dyes or dye precursors.

EXAMPLE 1 (comparative example)

A subbed water-resistant paper support consisting of a paper sheet of 110 g/sq.m coated at both sides with a polyethylene stratum of 15 g/sq.m was treated with a corona discharge and was coated at one side with a first layer, containing the following ingredients, the amounts relating to 1 sq.m of material:

| (1) gelatin | 1.5 g |
|---|---|
| cyan dye-providing IHR-compound C (structure after Table 2) | 0.25 g |
| silver chloride expressed as AgNO$_3$ (applied from a gelatin-silver chloride emulsion) | 0.50 g |
| ED compound 1: 2,5-bis(1',1',3'-tetramethylbutyl)-hydroquinone | 0.103 g |
| Said first layer was covered with a second layer containing per sq. m: | |
| gelatin | 6.00 g |
| 1-phenyl-4-methyl-3-pyrazolidinone as ETA-compound | 0.114 g |

PROCESSING

A sheet of the obtained photographic material was exposed through a grey wedge having a constant 0.1 and thereupon contacted for 1 minute with the receptor material described hereinafter in the COPYPROOF CP 38 (trade name) diffusion transfer processing apparatus containing in its tray an aqueous solution comprising per liter:

| sodium hydroxide | 25 g |
|---|---|
| sodium orthophosphate | 25 g |
| cyclohexane dimethanol | 25 ml |
| methyl, propyl-propane diol | 25 ml |
| potassium bromide | 1 g |
| potassium iodide | 2 g |
| sodium thiosulphate | 2 g |
| distilled water up to | 1000 ml |

COMPOSITION OF THE RECEPTOR MATERIAL

To the same support as described for the above light-sensitive material a coating for forming an image-receiving layer having the following composition was applied per sq.m:

| gelatin | 5 g |
| --- | --- |
| triphenyl-n-hexadecylphosphonium bromide | 2 g |

The minimum and maximum optical density results after said 1 minute contact time are listed in Table 2 following the Examples.

EXAMPLE 2 (comparative example)

Example 1 was repeated with the difference, however, that instead of ED-compound 1, ED-compound 2 having the following structural formula:

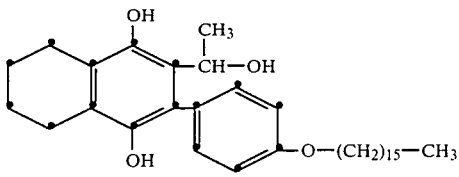

in an amount of 0.162 g was used.

EXAMPLE 3 (comparative example)

Example 1 was repeated with the difference, however, that instead of ED-compound 1, ED-compound 3 being ascorbyl palmitate having the following structural formula:

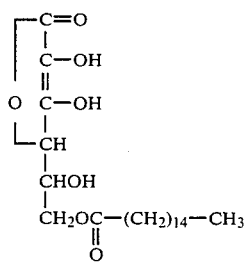

in an amount of 0.126 g was used.

EXAMPLE 4 (according to the present invention)

Example 1 was repeated with difference, however, that EDP-compound 14 of Table 1 in amount of 0.177 g was used.

EXAMPLE 5 (according to the present invention)

Example 1 was repeated with the difference, however, that EDP-compound 16 of Table 1 in amount of 0.180 g was used.

EXAMPLE 6 (according to the present invention)

Example 1 was repeated with the difference, however, that EDP-compound 2 of Table 1 in amount of 0.130 g was used.

EXAMPLE 7 (according to the present invention)

Example 1 was repeated with the difference, however, that EDP-compound 3 of Table 1 in an amount of 0.100 g was used.

TABLE 2

| ED compound | EDP-compound | Minimum density | Maximum density |
| --- | --- | --- | --- |
| 1 | — | 0.32 | 1.29 |
| 2 | — | 0.13 | 0.32 |
| 3 | — | 0.23 | 1.05 |
| — | 14 | 0.14 | 1.62 |
| — | 16 | 0.13 | 1.84 |
| — | 2 | 0.14 | 1.24 |
| — | 3 | 0.13 | 1.78 |

Structure of IHR-compound C:

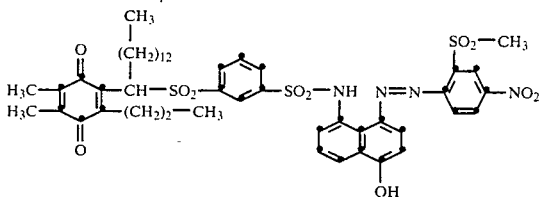

IHR-Compound C has been prepared in analogy to procedures described in the published European Patent Application No. 0004399.

We claim:

1. A photographic material comprising at least one light-sensitive silver halide emulsion layer containing at least one ballasted electron-donor precursor compound (EDP-compound) undergoing a cleavage reaction by alkaline hydrolysis to yield an electron-donor compound (ED-compound) capable of donating electrons to an electron-accepting oxidized silver halide developing agent, wherein said EDP-compound corresponds to the general formula:

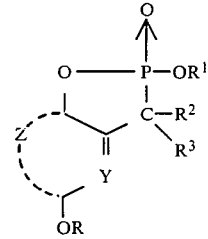

wherein:

R represents hydrogen or a substituent which on hydrolytic removal allows the replacement of R by H, $R^1$, $R^2$ and $R^3$ (same or different) represent a hydrocarbon group or $R^3$ represents hydrogen, and Z and Y represent the necessary atoms to close a benzene ring or Z and Y represent the necessary atoms to form a fused ring system including said benzene ring, at least one of $R^1$, $R^2$, $R^3$, Z and Y being or including a ballast group making said EDP-compound non-diffusing in a hydrophilic colloid layer when permeated by an alkaline aqueous liquid.

2. Photographic silver halide material according to claim 1, wherein said EDP-compund corresponds to the following general formula:

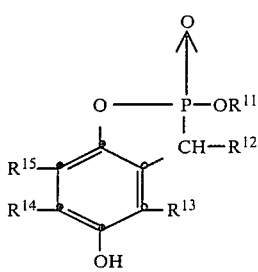

wherein: each of
R[11] and R[12] represent a hydrocarbon group, and
each of R[13], R[14] and R[15] (same or different) represent a hydrocarbon group, a halogen atom or an alkoxy group, or at least one of R[13], R[14] and R[15] together represents hydrogen, or R[14] and R[15] together represent the necessary atoms to form a fused homocyclic ring, at least one of R[11] to R[15] containing a carbon chain of at least 8 carbon atoms.

3. Photographic material according to claim 1, wherein the EDP-compound is present in a colour photographic silver halide material containing a plurality of differently spectrally sensitized silver halide emulsion layers.

4. Photographic material according to claim 1, wherein the EDP-compound is present in an interlayer between two silver halide emulsion layers.

5. Photographic material according to claim 1, wherein the photographic material is suited for dye diffusion transfer imaging and comprises a support carrying at least one alkali-permeable silver halide hydrophilic colloid emulsion layer which contains said EDP-compound and an IHR-compound which is immobile in an alkali-permeable colloid medium when contacted with an alkaline liquid and which contains a dye moiety and a ballast group, said IHR-compound being capable of being reduced by a silver halide developing agent and in reduced state being capable of releasing said dye moiety by alkaline hydrolysis.

6. Photographic material according to claim 5, wherein the IHR-compound which becomes cleavable in reduced state is a compound capable of undergoing an electron-accepting nucleophilic displacement reaction in alkaline liquid whereby a diffusible dye is released.

7. Photographic material according to claim 5, wherein the IHR-compound which becomes cleavable in reduced state is a compound capable of being split in an alkaline liquid into a ballasted quinone methide compound and a diffusible dye.

8. A photographic material according to claim 5, wherein said material comprises a support carrying red-, green- and blue-sensitive silver halide emulsion layers, each of said emulsion layers containing said IHR-compound that is initially immobile in an alkali-permeable colloid medium, and which is capable of releasing on cleaving a cyan, magenta and yellow dye, respectively.

9. A photographic material according to claim 5, wherein said material comprises one or more photosensitive silver halide emulsion layers, a supported non-light-sensitive receptor layer, and an alkali-permeable light-reflective opaque layer between and integral with said silver halide emulsion layer(s) and said supported receptor layer.

10. An image receiving material useful in diffusion-transfer-reversal processing with exposed silver halide emulsion layer(s), wherein said material contains in a water-permeable binder layer an EDP-compound corresponding to the general formula:

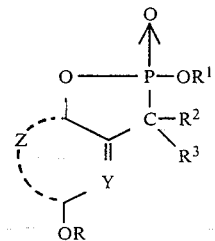

wherein:
R represents hydrogen or a substituent which an hydrolytic removal allows the replacement of R by H,
R[1], R[2] and R[3] (same or different) represent a hydrocarbon group or R[3] represents hydrogen, and
Z and Y represent the necessary atoms to close a benzene ring, or Z and Y represent the necessary atoms to form a fused ring system including said benzene ring, at least one of R[1], R[2], R[3], Z and Y being or including a ballast group making said EDP-compound non-diffusing in a hydrophilic colloid layer when permeated by an alkaline aqueous liquid.

11. An electron donor precursor compound, according to the following general formula:

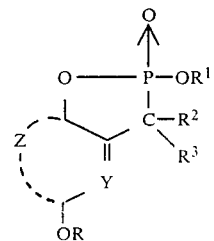

wherein:
R represents hydrogen or a substituent which on hydrolytic removal allows the replacement of R by H,
R[1], R[2] and R[3] (same or different) represent a hydrocarbon group or R[3] represents hydrogen, and
Z and Y represent the necessary atoms to close a benzene ring, or Z and Y represent the necessary atoms to form a fused ring system including said benzene ring, at least one of R[1], R[2], R[3], Z and Y being or including a ballast group making said EDP-compound non-diffusing in a hydrophilic colloid layer when permeated by an alkaline aqueous liquid.

* * * * *